(12) United States Patent
Saito

(10) Patent No.: US 12,383,125 B2
(45) Date of Patent: Aug. 12, 2025

(54) ENDOSCOPE SYSTEM AND METHOD OF OPERATING THE SAME

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 490 days.

(21) Appl. No.: 17/716,550

(22) Filed: Apr. 8, 2022

(65) Prior Publication Data

US 2022/0225865 A1 Jul. 21, 2022

Related U.S. Application Data

(63) Continuation of application No. PCT/JP2020/036673, filed on Sep. 28, 2020.

(30) Foreign Application Priority Data

Oct. 9, 2019 (JP) .................................. 2019-186240

(51) Int. Cl.
A61B 1/04 (2006.01)
A61B 1/05 (2006.01)
(Continued)

(52) U.S. Cl.
CPC ................ *A61B 1/044* (2022.02); *A61B 1/05* (2013.01); *A61B 5/14552* (2013.01); *A61B 5/1459* (2013.01); *A61B 5/6847* (2013.01)

(58) Field of Classification Search
CPC .......... A61B 1/000094; A61B 1/00057; A61B 1/044; A61B 1/045; A61B 1/05;
(Continued)

(56) References Cited

U.S. PATENT DOCUMENTS

2013/0033616 A1* 2/2013 Kaizu .................. H04N 25/583
348/222.1
2013/0345517 A1 12/2013 Morimoto et al.
(Continued)

FOREIGN PATENT DOCUMENTS

JP 2007-307225 A 11/2007
JP 2014-301 A 1/2014
(Continued)

OTHER PUBLICATIONS

International Preliminary Report on Patentability and English translation of the Written Opinion of the International Searching Authority for International Application No. PCT/JP2020/036673, dated Apr. 21, 2022.
(Continued)

*Primary Examiner* — Shahan Ur Rahaman
(74) *Attorney, Agent, or Firm* — Birch, Stewart, Kolasch & Birch, LLP

(57) ABSTRACT

An endoscope system includes a processor, and the processor acquires a plurality of spectral images for calculation of oxygen saturation that are used to calculate oxygen saturation of an object to be observed and spectral images for correction that are used to calculate correction values to be used to correct the oxygen saturation, creates a linearity correction table that is used to linearize a relationship between an amount of light incident on an image sensor and pixel values of the spectral images for correction, and calculates the correction values using the spectral images for correction that have been subjected to linearity correction using the linearity correction table.

10 Claims, 7 Drawing Sheets

(51) Int. Cl.
*A61B 5/00* (2006.01)
*A61B 5/1455* (2006.01)
*A61B 5/1459* (2006.01)

(58) Field of Classification Search
CPC . A61B 1/0638; A61B 5/0075; A61B 5/14552; A61B 5/1459; A61B 5/6847
See application file for complete search history.

(56) References Cited

U.S. PATENT DOCUMENTS

| | | | |
|---|---|---|---|
| 2014/0012112 A1 | 1/2014 | Kaku et al. | |
| 2016/0192834 A1* | 7/2016 | Niida | A61B 1/00009 600/109 |
| 2017/0311779 A1* | 11/2017 | Nakajima | A61B 1/00006 |
| 2018/0228347 A1* | 8/2018 | Yamamoto | A61B 1/00057 |
| 2018/0235527 A1 | 8/2018 | Yamamoto | |
| 2020/0020726 A1* | 1/2020 | Anas | H04N 25/78 |

FOREIGN PATENT DOCUMENTS

| | | |
|---|---|---|
| JP | 2014-14439 A | 1/2014 |
| JP | 2015-85097 A | 5/2015 |
| JP | 2017-108982 A | 6/2017 |
| JP | 2017-108983 A | 6/2017 |
| JP | 2017-148432 A | 8/2017 |
| JP | 2018-175762 A | 11/2018 |

OTHER PUBLICATIONS

International Search Report for International Application No. PCT/JP2020/036673, dated Dec. 8, 2020, with English translation.

\* cited by examiner

B3 IMAGE

ENDOSCOPE SYSTEM AND METHOD OF OPERATING THE SAME

CROSS-REFERENCE TO RELATED APPLICATIONS

This application is a Continuation of PCT International Application No. PCT/JP2020/036673 filed on 28 Sep. 2020, which claims priority under 35 U.S.C § 119(a) to Japanese Patent Application No. 2019-186240 filed on 9 Oct. 2019. The above application is hereby expressly incorporated by reference, in its entirety, into the present application.

BACKGROUND OF THE INVENTION

1. Field of the Invention

The present invention relates to an endoscope system that obtains the oxygen saturation of an object to be observed and a method of operating the endoscope system.

2. Description of the Related Art

An endoscope system, which picks up the image of an object to be observed in a living body, is widely used in a medical field. Since a correlation between oxygen saturation and a lesion area has been known, a diagnosis using oxygen saturation has also been made in recent years. In the diagnosis using oxygen saturation, the oxygen saturation of the object to be observed is calculated on the basis of a plurality of spectral images, which are obtained in a case where an affected area is irradiated with illumination light for oxygen saturation of which the light absorption coefficient is changed depending on oxygen saturation, and an oxygen saturation image in which the oxygen saturation is shown as an image is displayed on a monitor.

In a case where oxygen saturation is calculated, signal ratios between different spectral images are used as signal ratios obtained from calculation processing based on the plurality of spectral images. Since the slight variation of the signal ratio to be input becomes the noise of oxygen saturation to be output, the amount of light emitted from a light source unit, which emits illumination light for oxygen saturation, needs to be strictly controlled in terms of hardware. Further, in an endoscope system that calculates oxygen saturation, it is known that image correction values are calculated from images obtained from pre-image pickup and images for calculation of oxygen saturation are corrected using the calculated image correction values (JP2017-108983A (corresponding to US2018/235527A1)). In addition, in an endoscope system that does not calculate oxygen saturation, it is known that a set light amount data table is corrected to perform table correction for linearizing a relationship between the values of the set amounts of light emitted a green LED and a violet LED and signal values (pixel values) (JP2017-148432A).

SUMMARY OF THE INVENTION

With regard to an endoscope system that obtains oxygen saturation, not only the amount of light emitted from a light source needs to be strictly controlled in terms of hardware but also a technique for correcting the individual difference of an image sensor mounted on an endoscope is also important.

In general, a pixel value, which is the output signal of the image sensor, shows a substantially linear response to the amount of incident light to be input. However, depending on the range of the amount of incident light to be input and the range of the pixel value to be output, there may be a range in which response characteristics are slightly non-linear. Specific nonlinearity of such response characteristics varies depending on the individual image sensor. In a case where the response characteristics of the image sensor are non-linear, a ratio between pixel values in different spectral ranges (so-called signal ratio) deviates from a constant value even through illumination light having a constant intensity ratio for each wavelength range is emitted. As a result, the value of oxygen saturation calculated on the basis of a ratio between pixel values in different spectral ranges also has an error depending on the nonlinearity of the response characteristics of the image sensor.

An object of the present invention is to provide an endoscope system that can calculate accurate oxygen saturation by correcting an error caused by non-linear response characteristics of an image sensor and a method of operating the endoscope system.

An endoscope system according to an aspect of the present invention comprises: an endoscope that includes an image sensor picking up an image of an object to be observed; and a processor. The processor uses the endoscope to acquire a plurality of spectral images for calculation of oxygen saturation that are used to calculate oxygen saturation of the object to be observed and spectral images for correction that are used to calculate correction values to be used to correct the oxygen saturation, creates a linearity correction table that is used to linearize a relationship between an amount of light incident on the image sensor and pixel values of the spectral images for correction, and calculates the correction values using the spectral images for correction that have been subjected to linearity correction using the linearity correction table.

It is preferable that the processor calculates signal ratios, which are correlated with the oxygen saturation, from the plurality of spectral images for calculation of oxygen saturation, calculates the oxygen saturation using the signal ratios, and calculates the correction values that are used to correct the signal ratios.

It is preferable that white balance correction data, which is used for correction of white balance, is provided and the processor creates the linearity correction table using the white balance correction data.

It is preferable that the processor creates the linearity correction table in which a ratio between pixel values of a first color pixel and a second color pixel of the spectral image for correction subjected to white balance correction is associated with a pixel value of the first color pixel of the spectral image for correction not yet subjected to white balance correction.

It is preferable that the first color pixel is a blue pixel and the second color pixel is a green pixel.

It is preferable that the processor creates the linearity correction table using white balance correction data that are obtained in a case where an image of a reference plate is picked up using green light.

It is preferable that the processor causes a ratio between a pixel value of the first color pixel receiving the green light and a pixel value of the second color pixel receiving the green light to be associated with a pixel value of the first color pixel of the spectral image for correction not yet subjected to white balance correction.

It is preferable that a plurality of the white balance correction data, which are acquired while emission intensity of illumination light is changed, are provided and the processor creates the linearity correction table using the plurality of white balance correction data.

It is preferable that, in a case where correction data acquisition regions are set at a plurality of positions in one image for white balance correction and the white balance correction data are acquired in each of the correction data acquisition regions, the processor creates the linearity correction table using a plurality of the white balance correction data acquired from the one image for white balance correction.

A method of operating an endoscope system according to another aspect of the present invention is a method of operating an endoscope system including an endoscope that includes an image sensor picking up an image of an object to be observed, and a processor. The method comprises a step of causing the processor to use the endoscope to acquire a plurality of spectral images for calculation of oxygen saturation that are used to calculate oxygen saturation of the object to be observed and spectral images for correction that are used to calculate correction values to be used to correct the oxygen saturation, a step of causing the processor to create a linearity correction table that is used to linearize a relationship between an amount of light incident on the image sensor and pixel values of the spectral images for correction, and a step of causing the processor to calculate the correction values using the spectral images for correction that have been subjected to linearity correction using the linearity correction table.

According to the endoscope system and the method of operating the endoscope system of the aspects of the present invention, it is possible to calculate accurate oxygen saturation by correcting an error caused by non-linear response characteristics of an image sensor.

DESCRIPTION OF THE PREFERRED EMBODIMENTS

Figure 1:
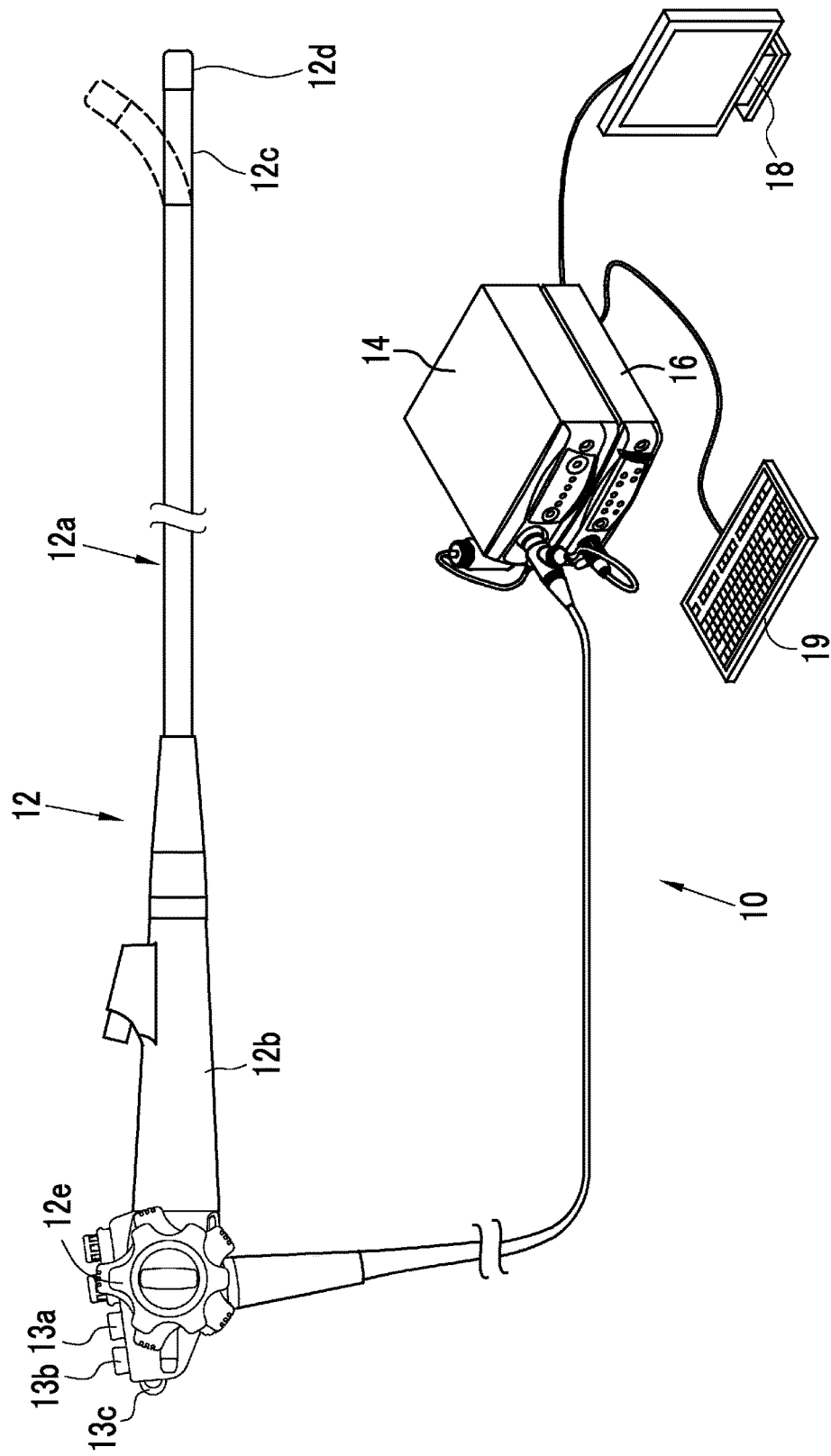
FIG. 1 is a diagram showing the appearance of an endoscope system.

As shown in FIG. 1, an endoscope system 10 according to a first embodiment includes an endoscope 12, a light source device 14, a processor device 16, a monitor 18 serving as a display unit, and a user interface 19. The endoscope 12 includes an image sensor 48 (see FIG. 2) that picks up the image of an object to be observed. The endoscope 12 is optically connected to the light source device 14 and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. The bendable part 12c is bent in a case where angle knobs 12e of the operation part 12b are operated. As a result of the bending of the bendable part 12c, the distal end part 12d faces in a desired direction. The distal end part 12d is provided with a jet port (not shown) that jets air, water, and the like toward an object to be observed.

Further, the operation part 12b is provided with a mode changeover switch 13a, a freeze switch 13b, and a zoom operation part 13c in addition to the angle knobs 12e. The mode changeover switch 13a is used for an operation for switching an observation mode. The endoscope system 10 has a normal mode, a special mode, and a calibration mode. The normal mode is an observation mode in which an image having a natural color tone (hereinafter, referred to as a normal image) obtained from the image pickup of the object to be observed using white light as illumination light is displayed on the monitor 18.

The special mode is an oxygen saturation observation mode in which the oxygen saturation of the object to be observed is calculated and displayed. In the oxygen saturation observation mode, the oxygen saturation of the object to be observed is calculated using a plurality of spectral images obtained from the image pickup of the object to be observed and an image in which the value of the calculated oxygen saturation is shown using a pseudo color (hereinafter, referred to as an oxygen saturation image) is generated and displayed on the monitor 18. White balance correction data to be used for white balance correction processing and a linearity correction table to be used for linearity correction are created in the calibration mode.

The freeze switch 13b is a switch that is used to give a static image-acquisition instruction to the processor device 16. The processor device 16 stores static images according to the static image-acquisition instruction.

The processor device 16 is electrically connected to the monitor 18 and the user interface 19. The monitor 18 outputs and displays the image of each observation mode, image information accessory to the image, and the like. The user interface 19 includes a keyboard and the like, and receives input operations, such as function settings. A mouse and the like may be provided as the user interface 19 in addition to the keyboard. An external recording unit (not shown) in which images, image information, and the like are recorded may be connected to the processor device 16.

Figure 2:
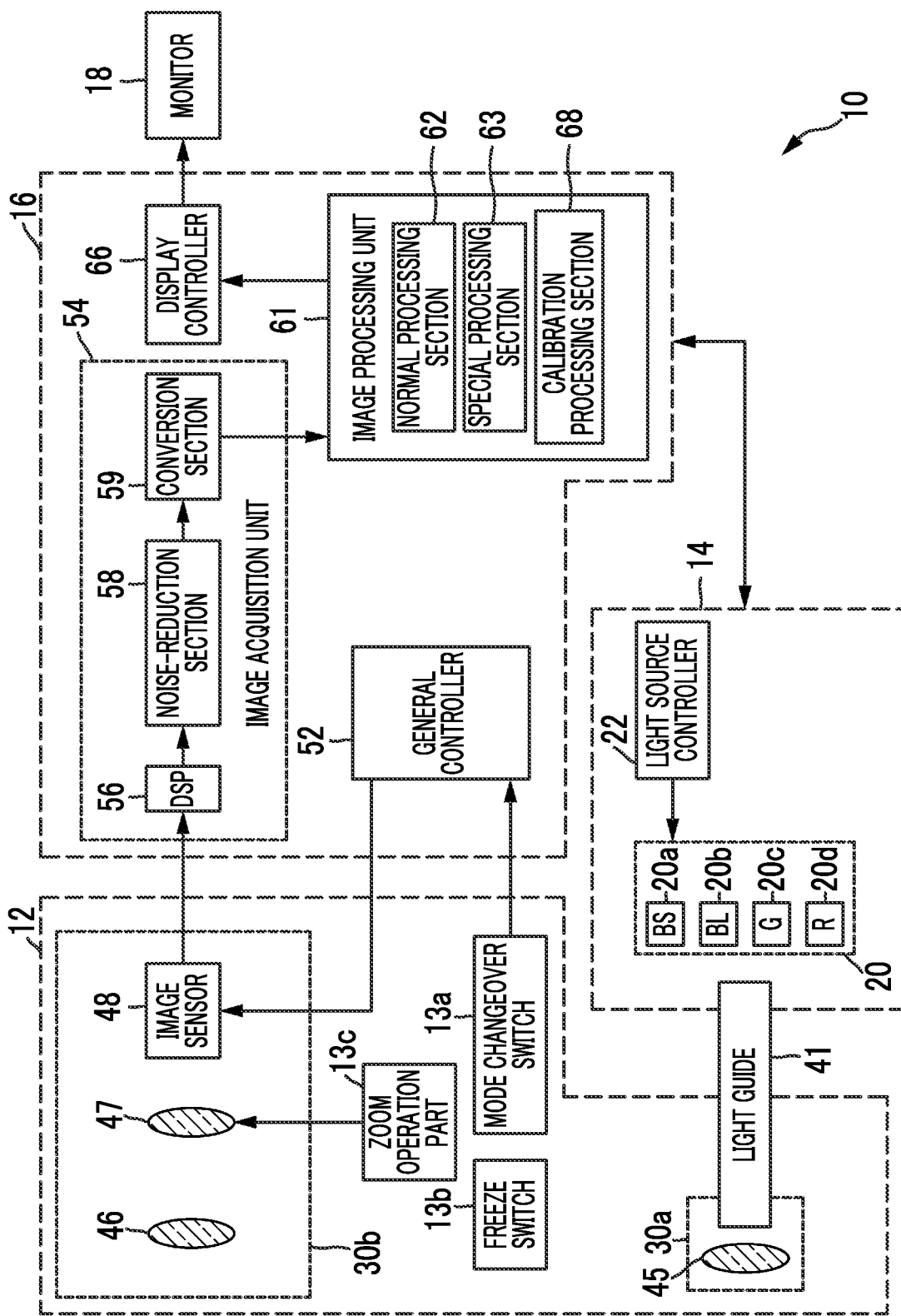
FIG. 2 is a block diagram showing the functions of the endoscope system.

As shown in FIG. 2, the light source device 14 comprises a light source unit 20 that emits illumination light and a light source controller 22 that controls the drive of the light source unit 20.

The light source unit 20 comprises four semiconductor light sources, that is, a BS light source 20a, a BL light source 20b, a G light source 20c, and an R light source 20d. In this embodiment, all of the BS light source 20a, the BL light source 20b, the G light source 20c, and the R light source 20d are light emitting diodes (LEDs). A combination of a laser diode (LD), a phosphor, and a band-limiting filter; a combination of a lamp, such as a xenon lamp, and a band-limiting filter; and the like can be used in the light source unit 20 instead of these LEDs.

Figure 3:
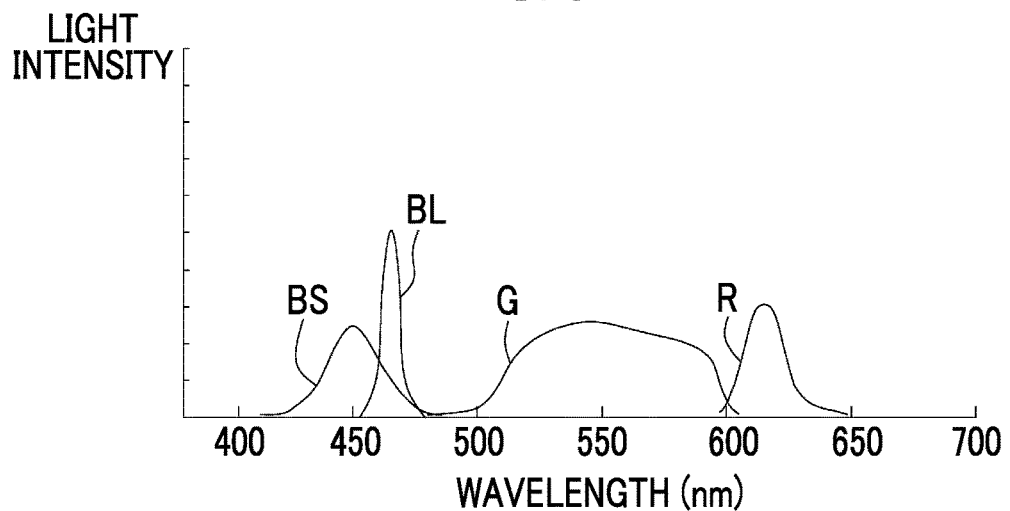
FIG. 3 is a graph showing the emission spectra of first blue light, second blue light, green light, and red light.

As shown in FIG. 3, the BS light source 20*a* is a blue light source that emits first blue light BS of which the central wavelength (peak wavelength) is in the range of about 450±10 nm and the wavelength range is in the range of about 420 nm to 500 nm. The BL light source 20*b* is a blue light source that emits so-called blue narrow-band light (hereinafter, referred to as second blue light BL) of which the central wavelength (peak wavelength) and the wavelength range are in the range of about 470±10 nm. The G light source 20*c* is a green light source that emits green light G of which the central wavelength (peak wavelength) is in the range of about 540±20 nm and the wavelength range is in the range of about 480 nm to 600 nm. The R light source 20*d* is a red light source that emits red light R of which the central wavelength (peak wavelength) is in the range of about 620±20 nm and the wavelength range is in the range of about 600 nm to 650 nm.

The light source controller 22 independently controls the timings of the turning on or off of the respective light sources 20*a* to 20*d* of the light source unit 20, the amounts of light emitted at the times of turning on thereof, and the like. Due to the control of the light source controller 22, the light source unit 20 emits illumination light for normal observation to be used in the normal mode and illumination light for oxygen saturation observation to be used in the oxygen saturation observation mode.

In the case of the normal mode, the light source controller 22 simultaneously turns on the BS light source 20*a*, the G light source 20*c*, and the R light source 20*d*. For this reason, illumination light for normal observation is white light that includes first blue light BS, green light and red light R. In this embodiment, in the case of the normal mode, the light source unit 20 constantly emits the white light but may emit the white light at an image pickup timing (hereinafter, referred to as an image pickup frame) of the object to be observed.

Figure 4:
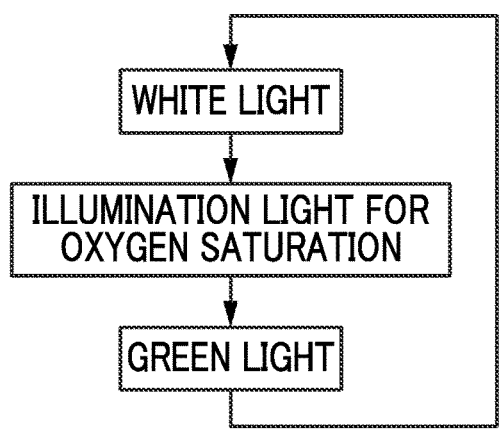
FIG. 4 is a diagram illustrating a light emission pattern in an oxygen saturation observation mode.

In the cases of the oxygen saturation observation mode and the calibration mode, the light source controller 22 alternately and repeatedly turns on or off the respective light sources 20*a* to 20*d* in a first pattern, a second pattern, and a third pattern. The first pattern is a pattern in which the BS light source 20*a*, the G light source 20*c*, and the R light source 20*d* are simultaneously turned on. In the case of the first pattern, white light including first blue light BS, green light and red light R is emitted as illumination light. On the other hand, the second pattern is a pattern in which the BL light source 20*b*, the G light source 20*c*, and the R light source 20*d* are simultaneously turned on. For this reason, illumination light for oxygen saturation including second blue light BL, green light and red light R is emitted in the case of the second pattern. In the third pattern, the G light source 20*c* is turned on alone. For this reason, green light G is emitted as illumination light in the case of the third pattern. Accordingly, in the oxygen saturation observation mode and the calibration mode, as shown in FIG. 4, white light, illumination light for oxygen saturation, and green light are alternately and repeatedly emitted for, for example, each image pickup frame in accordance with an image pickup frame.

In the calibration mode, it is sufficient that the light sources are turned on in each of the first pattern, the second pattern, and the third pattern at least once but the light sources are sequentially and repeatedly turned on as necessary. In this embodiment, the light sources are automatically, alternately, and repeatedly turned on or off in the first pattern, the second pattern, and the third pattern until the calibration mode ends.

Illumination light emitted from the light source unit 20 is incident on a light guide 41 (see FIG. 2). The light guide 41 is built in the endoscope 12 and a universal cord, and transmits illumination light to the distal end part 12*d* of the endoscope 12. The universal cord is a cord that connects the endoscope 12 to the light source device 14 and the processor device 16. A multimode fiber can be used as the light guide 41. For example, a thin fiber cable of which a total diameter of a core diameter of 105 μm, a cladding diameter of 125 μm, and a protective layer forming a covering is in the range of φ 0.3 to 0.5 mm can be used.

The distal end part 12*d* of the endoscope 12 is provided with an illumination optical system 30*a* and an image pickup optical system 30*b*. The illumination optical system 30*a* includes an illumination lens 45, and the object to be observed is irradiated with illumination light through the illumination lens 45. The image pickup optical system 30*b* includes an objective lens 46, a zoom lens 47, and an image sensor 48. The image sensor 48 picks up the image of the object to be observed using the reflected light and the like (including scattered light, fluorescence emitted from the object to be observed, fluorescence caused by a medicine given to the object to be observed, or the like) of illumination light returning from the object to be observed through the objective lens 46 and the zoom lens 47. The zoom lens 47 is moved by the operation of the zoom operation part 13*c* and increases or reduces the size of the object to be observed of which the image is to be picked up by the image sensor 48.

Figure 5:
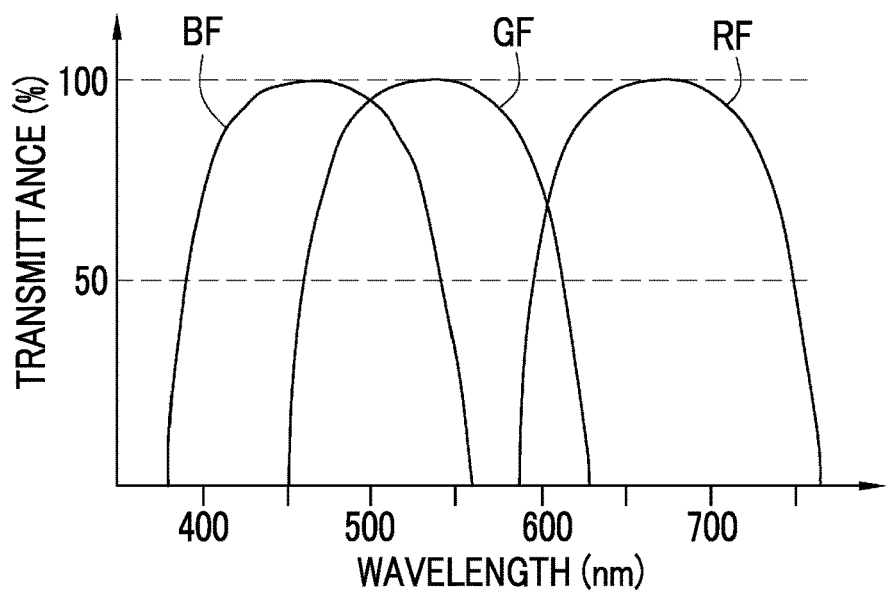
FIG. 5 is a graph showing the spectral characteristics of color filters.

The image sensor 48 is a primary color sensor, and comprises three types of pixels, that is, B pixels (blue pixels) including blue color filters, G pixels (green pixels) including green color filters, and R pixels (red pixels) including red color filters. As shown in FIG. 5, the blue color filter mainly transmits light of a blue light wavelength range, specifically, light of which the wavelength range is in the range of 380 to 560 nm. The transmittance of the blue color filter BF has a peak near a wavelength of 460 to 470 nm. The green color filter GF mainly transmits light of a green light wavelength range, specifically, light of which the wavelength range is in the range of 460 to 470 nm. The red color filter RF mainly transmits light of a red light wavelength range, specifically, light of which the wavelength range is in the range of 580 to 760 nm.

In a case where the image of the object to be observed is picked up by the image sensor 48, three types of spectral images, that is, a B image (blue image) obtained from the image pickup in the B pixel, a G image (green image) obtained from the image pickup in the G pixel, and an R image (red image) obtained from the image pickup in the R pixel can be obtained at the maximum in a single image pickup. Since illumination light for normal observation to be used is white light in the case of the normal mode, Bc images, Gc images, and Rc images are obtained. The Bc image is an image that is obtained from the image pickup of the object to be observed mainly using the reflected light and the like of first blue light BS, and the Gc image is an image that is obtained from the image pickup of the object to be observed mainly using the reflected light and the like of green light G Likewise, the Rc image is an image that is obtained from the image pickup of the object to be observed mainly using the reflected light and the like of red light R.

On the other hand, in the oxygen saturation observation mode and the calibration mode, B1 images, G1 images, and R1 images are acquired as spectral images in a frame where white light is emitted, B2 images, G2 images, and R2 images are acquired as spectral images in a frame where illumination light for oxygen saturation is emitted, and B3 images and G3 images are acquired as spectral images in a frame where green light G is emitted. The B1 image, the G1 image, and the R1 image are the same as the Bc image, the Gc image, and the Rc image. The B2 image is an image that is obtained from the image pickup of the object to be observed mainly using the reflected light and the like of second blue light BL. The G2 image is an image that is obtained from the image pickup of the object to be observed mainly using the reflected light and the like of green light G Likewise, the R2 image is an image that is obtained from the image pickup of the object to be observed mainly using the reflected light and the like of red light R. The B3 image is an image that is obtained from the image pickup of the object to be observed performed using green light G by the B pixel in a case where the sub-sensitivity of the blue color filter BF is used. The G3 image is an image that is obtained from the image pickup of the object to be observed performed using green light G by the G pixel.

Figure 6:
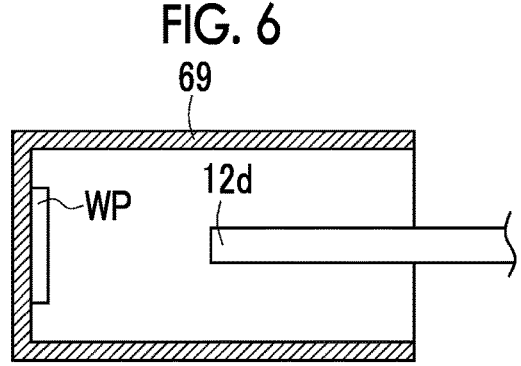
FIG. 6 is a diagram illustrating a calibration device.

However, in the calibration mode, the image of a reference reflective plate having predetermined spectral reflection characteristics is picked up instead of the image of the object to be observed. In this embodiment, the endoscope 12 is inserted into a calibration device 69 as shown in FIG. 6 and picks up the image of a white reference reflective plate (hereinafter, referred to a reference white plate WP). For this reason, the B1 image, the G1 image, the R1 image, the B2 image, the G2 image, the R2 image, the B3 image, and the G3 image obtained in the calibration mode are images that are obtained from the image pickup of "reference white plate WP" instead of the object to be observed.

A charge coupled device (CCD) sensor or a complementary metal oxide semiconductor (CMOS) sensor can be used as the image sensor 48. Further, the image sensor 48 of this embodiment is a primary color sensor, but a complementary color sensor can also be used as the image sensor 48. The complementary color sensor includes, for example, cyan pixels provided with cyan color filters, magenta pixels provided with magenta color filters, yellow pixels provided with yellow color filters, and green pixels provided with green color filters. In a case where the complementary color sensor is used, images obtained from the respective color pixels described above can be converted into the B image, the G image, and the R image by complementary color-primary color conversion. Further, a monochrome sensor not provided with color filters can be used as the image sensor 48 instead of the color sensor. In this case, the images having the respective colors can be obtained from the sequential image pickup of the object to be observed using illumination light having the respective colors, such as B, and R.

The processor device 16 includes a general controller 52, an image acquisition unit 54, an image processing unit 61, and a display controller 66 (see FIG. 2.)

The general controller 52 controls each unit provided in the processor device 16. The general controller 52 performs a control corresponding to each mode on the basis of a mode changeover signal output from the mode changeover switch 13a. Further, the general controller 52 controls the endoscope 12 and the light source device 14. The general controller 52 controls the irradiation timing of illumination light by controlling the light source controller 22 of the light source device 14. Furthermore, the general controller 52 controls an image pickup timing by controlling the image sensor 48 of the endoscope 12.

The image acquisition unit 54 acquires the image of the object to be observed from the image sensor 48. In the case of the normal mode, the image acquisition unit 54 acquires Bc images, Gc images, and Rc images for each image pickup frame. In the cases of the oxygen saturation observation mode and the calibration mode, the image acquisition unit 54 acquires the B1 images, the G1 images, the R1 images, the B2 images, the G2 images, the R2 images, the B3 images, and the G3 images. Among these images, the B1 image, the B2 image, the G1 image, and the R1 image are a plurality of spectral images for calculation of oxygen saturation that are used to calculate the oxygen saturation of the object to be observed. Further, the B3 image and the G3 image are spectral images for correction that are used to calculate correction values to be used to correct oxygen saturation. That is, the image acquisition unit 54 acquires spectral images for calculation of oxygen saturation and the spectral images for correction in the oxygen saturation observation mode and the calibration mode.

Further, the image acquisition unit 54 includes a digital signal processor (DSP) 56, a noise-reduction section 58, and a conversion section 59, and performs various types of processing on the acquired images using these.

The DSP 56 performs various types of processing, such as defect correction processing, offset processing, gain correction processing, matrix processing, gamma conversion processing, demosaicing processing, and YC conversion processing, on the acquired images as necessary.

The defect correction processing is processing for correcting the pixel values of pixels corresponding to defective pixels of the image sensor 48. The offset processing is processing for reducing dark current components from the images subjected to the defect correction processing and setting an accurate zero level. The gain correction processing is processing for multiplying the images, which have been subjected to the offset processing, by gains to adjust the signal level of each image. The matrix processing is processing for improving the color reproducibility of the images subjected to the offset processing, and the gamma conversion processing is processing for adjusting the brightness and chroma saturation of the images subjected to the matrix processing. The demosaicing processing (also referred to as equalization processing or demosaicing) is processing for interpolating the pixel values of missing pixels, and is performed on the images subjected to the gamma conversion processing. The missing pixels are pixels that do not have pixel values since other color pixels are arranged in the image sensor 48 due to the arrangement of color filters. For example, since the B image is an image obtained from the image pickup of the object to be observed in the B pixel, pixels arranged at the positions of the G pixel and the R pixel of the image sensor 48 do not have pixel values. In the demosaicing processing, the B image is interpolated to generate the pixel values of pixels arranged at the positions of the G pixel and the R pixel of the image sensor 48. The YC conversion processing is processing for converting images, which have been subjected to the demosaicing processing, into luminance channels Y, color difference channels Cb, and color difference channels Cr.

The noise-reduction section 58 performs noise-reduction processing on the luminance channels Y, the color difference channels Cb, and the color difference channels Cr, using, for example, a moving average method, a median filtering method, or the like. The conversion section 59 converts the luminance channels Y, the color difference channels Cb, and the color difference channels Cr, which have been subjected to the noise-reduction processing, into images having the respective colors of B, and R, again.

The image processing unit 61 includes a normal processing section 62, a special processing section 63, and a calibration processing section 68. The normal processing section 62 operates in the normal mode; performs color conversion processing, color enhancement processing, and structure enhancement processing on the Bc images, the Gc images, and Rc images for one image pickup frame, which have been subjected to the above-mentioned various types of processing; and generates normal images. In the color conversion processing, 3×3-matrix processing, gradation transformation processing, and three-dimensional look up table (LUT) processing, and the like are performed on the images having the respective colors of B, and R. The color enhancement processing is processing for enhancing the color of an image, and the structure enhancement processing is processing for enhancing, for example, the tissue or structure of the object to be observed, such as blood vessels or a pit pattern. The display controller 66 sequentially acquires normal images from the normal processing section 62, converts the acquired normal images into a format that is suitable to be displayed, and sequentially outputs and displays the converted normal images on the monitor 18. Accordingly, in the case of the normal mode, a medical doctor or the like can observe the object to be observed using the video of the normal images.

The special processing section 63 operates in the oxygen saturation observation mode, and calculates oxygen saturation on the basis of the linearity correction table in addition to the B1 images, the G1 images, the R1 images, and the B2 images that are specific spectral images required for calculation of oxygen saturation. Further, the special processing section 63 creates an oxygen saturation image subjected to coloring processing or the like according to the calculated oxygen saturation.

Figure 7:
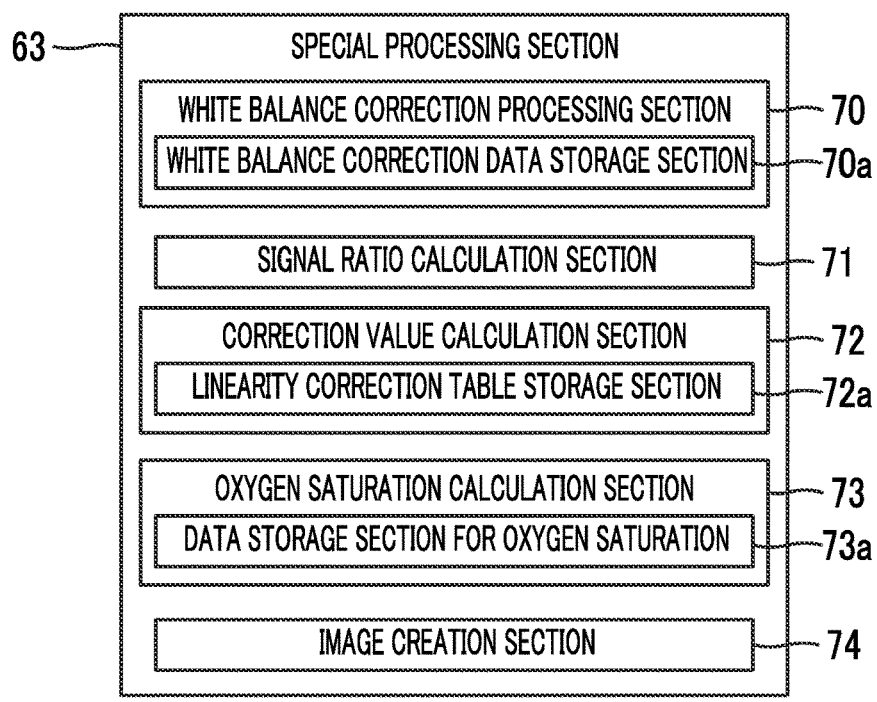
FIG. 7 is a block diagram showing the functions of a special processing section.

As shown in FIG. 7, the special processing section 63 comprises a white balance correction processing section 70, a signal ratio calculation section 71, a correction value calculation section 72, an oxygen saturation calculation section 73, and an image creation section 74. The white balance correction processing section 70 performs white balance correction processing on the B1 images, the G1 images, the R1 images, and the B2 images, which are specific spectral images, using the white balance correction data stored in a white balance correction data storage section 70a. The white balance correction data include white balance correction data NB1 for B1 image, white balance correction data NG1 for G1 image, white balance correction data NR1 for R1 image, white balance correction data NB2 for B2 image, white balance correction data NB3 for B3 image, white balance correction data NG3 for G3 image, and the like.

The B1 image is divided by the white balance correction data NB1 for B1 image in the white balance correction processing section 70, so that a B1 image subjected to white balance correction (B1*=B1/NB1) is obtained. Likewise, the G1 image is divided by the white balance correction data NG1 for G1 image, so that a G1 image subjected to white balance correction (G1*=G1/NG1) is obtained. Further, the R1 image is divided by the white balance correction data NR1 for R1 image, so that an R1 image subjected to white balance correction (R1*=R1/NR1) is obtained. Furthermore, the B2 image is divided by the white balance correction data NB2 for B2 image, so that a B2 image subjected to white balance correction (B2*=B2/NB2) is obtained. Likewise, the B3 image is divided by the white balance correction data NB3 for B3 image, so that a B3 image subjected to white balance correction (B3*=B3/NB3) is obtained. Further, the G3 image is divided by the white balance correction data NG3 for G3 image, so that a G3 image subjected to white balance correction (G3*=G3/NG3) is obtained.

The signal ratio calculation section 71 calculates "signal ratios", which are calculation values for calculation of oxygen saturation, by calculation processing based on the B1 image, the G1 image, the R1 image, and the B2 image (B1*, G1*, R1*, and B2*) that are specific spectral images subjected to white balance correction. That is, the signal ratio calculation section 71 calculates signal ratios, which are correlated with oxygen saturation, from the plurality of spectral images for calculation of oxygen saturation. Specifically, the signal ratio calculation section 71 calculates a signal ratio X (=ln(R1*/G1*)) by performing calculation that logarithmizes the R1 image subjected to white balance correction by dividing the R1 image subjected to white balance correction by the G1 image subjected to white balance correction. Further, the signal ratio calculation section 71 calculates a signal ratio Y (=ln(B2*/G1*)) by performing calculation that logarithmizes the B2 image subjected to white balance correction by dividing the B2 image subjected to white balance correction by the G1 image subjected to white balance correction.

The correction value calculation section 72 calculates correction values that are used to correct oxygen saturation. Further, the correction value calculation section 72 comprises a linearity correction table storage section 72a that stores the linearity correction table. Accordingly, in a case where the correction value calculation section 72 is to calculate the correction values, the correction value calculation section 72 uses the spectral images for correction that have been subjected to linearity correction using the linearity correction table.

The linearity correction table is a numerical value table that is used to correct the nonlinearity of response characteristics varying for each individual image sensor 48. That is, the linearity correction table is a numerical value table that is used to linearize a relationship between the amount of light incident on the image sensor 48 (the amount of light received by the image sensor 48) and the pixel values of the spectral images for correction.

Figure 8:
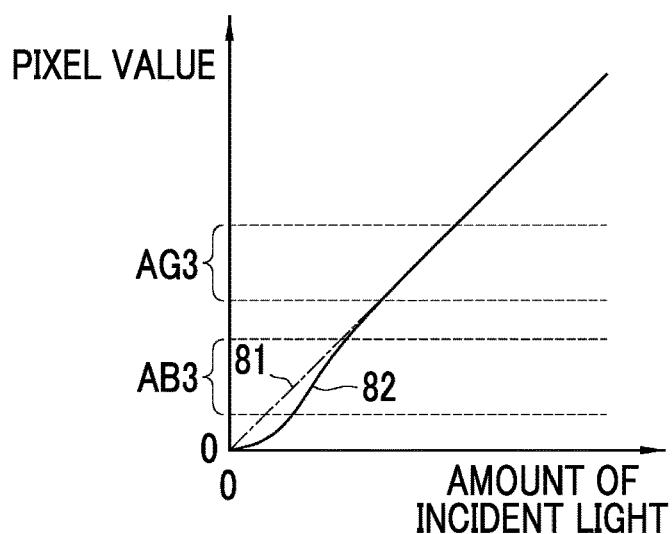
FIG. 8 is a graph showing the response characteristics of an image sensor.

As shown in FIG. 8, an input to the image sensor 48 is the amount of incident light and the output of the image sensor 48 is pixel values (an image that is a set of pixel values). Most of the response characteristics of the image sensor 48 between the amount of incident light and the pixel value are adjusted to be linear ideally like a graph 81 shown by a dashed-dotted line. However, it is difficult to strictly linearize the response characteristics of the image sensor 48, and the response characteristics of the image sensor 48 are non-linear in a part of the range of the amount of incident light and the pixel value actually like a graph 82 shown by a solid line. In particular, the response characteristics of the image sensor 48 are likely to be non-linear in a range where the amount of incident light and pixel value are small. For example, the response characteristics of the image sensor 48 are substantially linear in a range AG3 of a value that can be taken by the pixel value of the G3 image not yet subjected to white balance correction, but the response characteristics of the image sensor 48 are non-linear in a range AB3 of a value that can be taken by the pixel value of the B3 image not yet subjected to white balance correction. The linearity correction table is to correct of the deviation of a pixel value that is caused by the nonlinearity of the response characteristics of the image sensor 48 described above, and the pixel value of the spectral image for correction (particularly, the B3 image) is associated with a pixel value proportional to the current amount of incident light in the linearity correction table.

Figure 9:
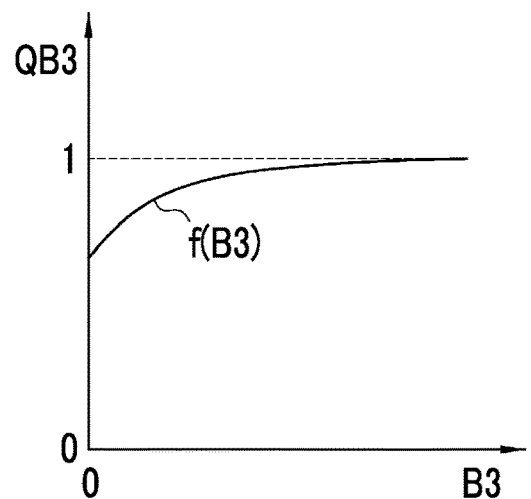
FIG. 9 is a graph showing a linearity correction table.

Specifically, in the linearity correction table, a ratio between the pixel values of a first color pixel and a second color pixel of the spectral image for correction subjected to white balance correction is associated with the pixel value of a first color pixel of the spectral image for correction not yet subjected to white balance correction. In this embodiment, the first color pixel is the B pixel and the second color pixel is the G pixel. Accordingly, as shown in FIG. 9, in the linearity correction table, a ratio QB3 (=B3*/G3*) between the pixel values of the B3 image (B3*) and the G3 image (G3*) subjected to white balance correction is associated with the pixel value (B3) of the B3 image not yet subjected to white balance correction. In an ideal case where the response characteristics of the image sensor 48 is linear in the entire range of the amount of incident light and the pixel value, the value of the ratio QB3 is "1" regardless of the pixel value (B3) of the B3 image not yet subjected to white balance correction. On the other hand, the value of the ratio QB3 deviates from "1" in the range of the amount of incident light and the pixel value where the response characteristics of the image sensor 48 is non-linear. Further, this deviation can be expressed by, for example, a function f(B3) in which the pixel value (B3) of the B3 image not yet subjected to white balance correction is used as a variable. The function f(B3) is a function that approximates the value of the ratio QB3 with regard to the pixel value (B3) of the B3 image not yet subjected to white balance correction, and is, for example, a polynomial, an exponential function, or the like.

First, the correction value calculation section 72 performs linearity correction on the B3 image (B3*), which has been subjected to white balance correction, using the linearity correction table. That is, the correction value calculation section 72 obtains a pixel value B3** (=B3*/f(B3)) of the B3 image, which has been subjected to linearity correction, for each pixel by dividing the pixel value of the B3 image subjected to white balance correction by the value of the function f(B3) that makes a calculation using the pixel value of the B3 image not yet subjected to white balance correction. After that, the correction value calculation section 72 calculates a signal ratio Z (=ln(B3**/G3*)) by performing calculation that logarithmizes the pixel value B3 of the B3 image subjected to linearity correction by dividing the pixel value B3 of the B3 image subjected to linearity correction by the pixel value G3* of the G3 image subjected to white balance correction.

Then, the correction value calculation section 72 obtains a correction value ΔY, which is to be added to the signal ratio Y, using the signal ratios X and Y, which are calculated by the signal ratio calculation section 71, and the signal ratio Z in order to correct oxygen saturation. In this embodiment, the correction value ΔY is a linear combination of the signal ratio X, the signal ratio Y, and the signal ratio Z, and coefficient $K_X$, $K_Y$, and $K_Z$ for the ratios are predetermined by experiments or the like. That is, "ΔY=$K_X$×X+$K_Y$×Y+$K_Z$×Z" is satisfied. The correction value ΔY can be a positive value or a negative value depending on specific individual response characteristics of the image sensor 48. Further, the correction value ΔY is a correction value that is used to directly correct the signal ratio Y. However, since the value of oxygen saturation is corrected as a result of the correction of the signal ratio Y using the correction value ΔY, the correction value ΔY is "a correction value that is used to correct oxygen saturation".

The oxygen saturation calculation section 73 calculates the oxygen saturation of the object to be observed using the signal ratios X and Y. Specifically, the oxygen saturation calculation section 73 calculates the oxygen saturation, which corresponds to the signal ratios X and Y, for each pixel with reference to a data storage section 73a for oxygen saturation in which a correlation between the signal ratios X and Y and oxygen saturation is stored. Further, the oxygen saturation calculation section 73 does not use the signal ratio Y as it is and uses a signal ratio Y* (=Y+ΔY) in which the correction value ΔY is added to the signal ratio Y to obtain accurate oxygen saturation from which the influence of the individual difference (the nonlinearity of response characteristics) of the image sensor 48 has been reduced.

Figure 10:
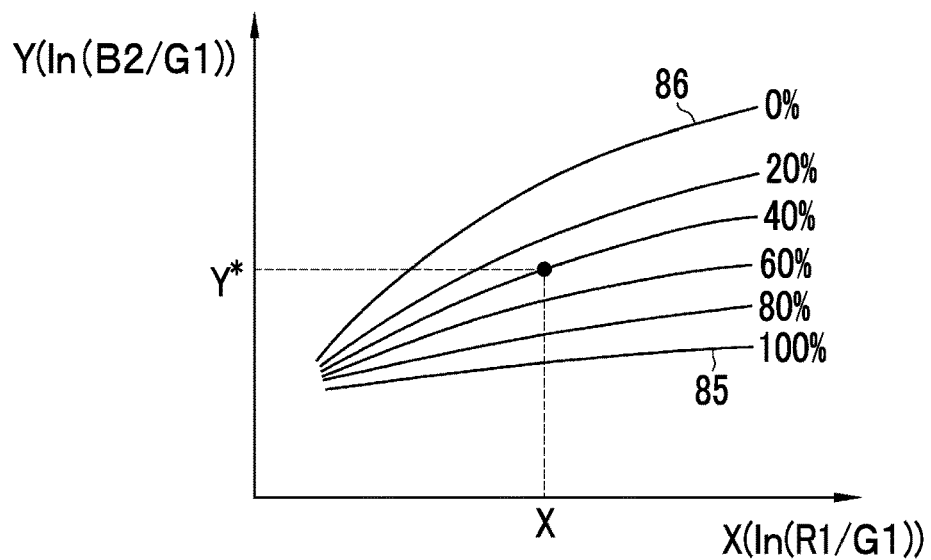
FIG. 10 is a diagram illustrating a relationship between oxygen saturation and a signal ratio X and a signal ratio Y.

With regard to the correlation stored in the data storage section 73a for oxygen saturation, isolines, which connect points where oxygen saturation has the same value, are formed in a substantially horizontal direction as shown in FIG. 10 in a feature space of which the vertical axis represents the signal ratio Y and the horizontal axis represents the signal ratio X. Further, the isoline is positioned on the lower side in the direction of the vertical axis as oxygen saturation is larger. For example, an isoline 85 on which oxygen saturation is 100% is positioned below an isoline 86 on which oxygen saturation is 0%.

For example, referring to the correlation stored in the data storage section 73a for oxygen saturation, oxygen saturation corresponding to the corrected signal ratios X and Y* is "40%". Accordingly, the oxygen saturation calculation section 73 calculates the oxygen saturation of a pixel corresponding to the signal ratios X and Y* as "40%".

The image creation section 74 creates an oxygen saturation image using oxygen saturation. Specifically, the image creation section 74 creates a normal image on the basis of the B1 image, the G1 image, and the R1 image and changes the color tone of the normal image according to oxygen saturation. For example, it is preferable that the image creation section 74 does not change the color tone of a pixel of the normal image where oxygen saturation exceeds 70% and displays the pixel as it is, but changes the color tone of a pixel of the normal image where oxygen saturation is 70% or less and displays the pixel. In a case where a color tone is to be changed, it is preferable that the color tone is closer to a cold color (for example, blue) as oxygen saturation is lower. The image creation section 74 may create an oxygen saturation image using oxygen saturation and a specific color image without creating a normal image. In this case, it is preferable that the image creation section 74 creates an oxygen saturation image using the luminance channel Y and the color difference channels Cr and Cb. For example, it is preferable that the luminance channel Y is assigned to G1 image signals and the color difference channels Cr and Cb are assigned according to oxygen saturation.

Figure 11:
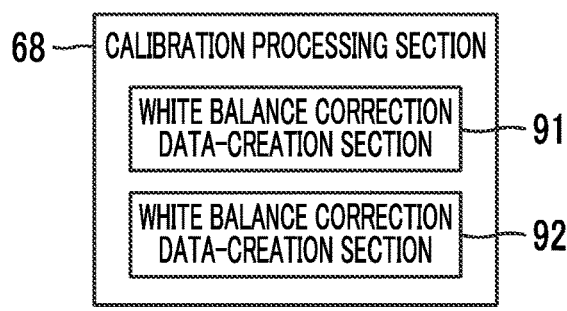
FIG. 11 is a block diagram showing the functions of a calibration processing section.

The calibration processing section 68 operates in the calibration mode and creates or calibrates the white balance correction data and/or the linearity correction table. For this purpose, as shown in FIG. 11, the calibration processing section 68 comprises a white balance correction data-creation section 91 and a linearity correction table-creation section 92.

Figure 12:
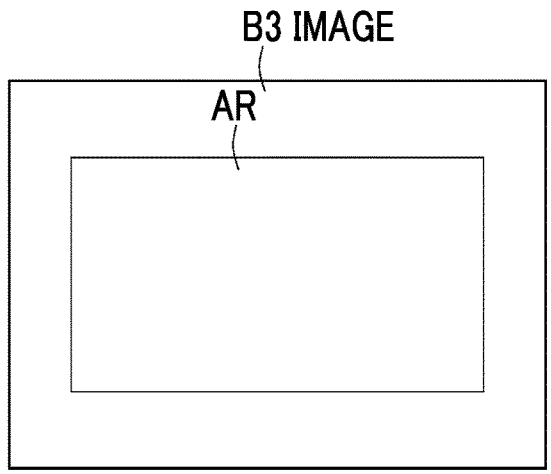
FIG. 12 is a diagram illustrating a correction data acquisition region.

The white balance correction data-creation section 91 acquires the B1 image, the G1 image, the R1 image, the B2 image, the G2 image, the R2 image, the B3 image, and the G3 image, which are obtained from the image pickup of the reference white plate WP instead of the object to be observed, in the calibration mode. Then, the white balance correction data-creation section 91 sets a rectangular correction data acquisition region AR shown in FIG. 12 in each of these respective images, and calculates the average values or the like (statistics, such as average values or medians) of the pixel values of the correction data acquisition regions AR. The average values or the like of the pixel values of the correction data acquisition regions AR of these respective images are defined as white balance correction data (NB1, NG1, NR1, NB2, NB3, NG3, and the like). The white balance correction data are stored in the white balance correction data storage section 70a. The shape of the correction data acquisition region AR may be a circular shape in addition to a rectangular shape.

The linearity correction table-creation section 92 creates the above-mentioned linearity correction table in the calibration mode, and stores the created linearity correction table in the linearity correction table storage section 72a. Specifically, the linearity correction table-creation section 92 acquires the B3 image not yet subjected to white balance correction and the B3 image and the G3 image subjected to white balance correction in the calibration mode, and creates the linearity correction table using these.

Accordingly, the linearity correction table-creation section 92 creates the linearity correction table using the white balance correction data. Further, the linearity correction table-creation section 92 creates the linearity correction table in which a ratio between the pixel values of the first color pixel and the second color pixel of the spectral image for correction subjected to white balance correction is associated with the pixel value of the first color pixel of the spectral image for correction not yet subjected to white balance correction. The linearity correction table-creation section 92 creates the linearity correction table using the white balance correction data that are obtained in a case where the image of a predetermined reference plate, such as reference white plate WP, is picked up using green light G Further, the linearity correction table-creation section 92 causes a ratio between the pixel value of the B pixel (first color pixel) receiving green light G and the pixel value of the G pixel (second color pixel) receiving green light G to be associated with the pixel value of the B pixel (first color pixel) of the B3 image that is a spectral image for correction not yet subjected to white balance correction.

Figure 13:
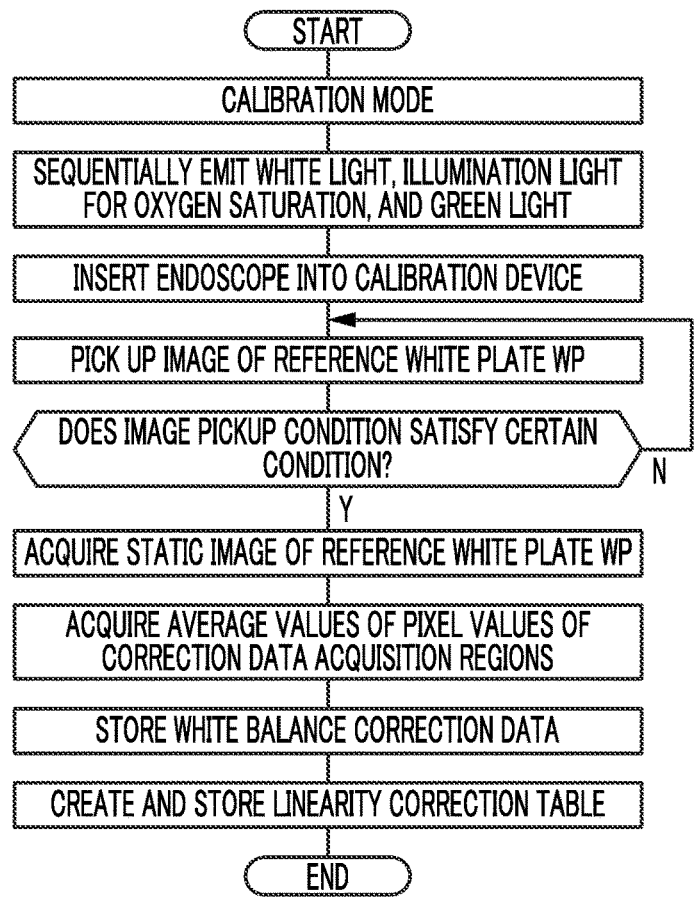
FIG. 13 is a flowchart of a calibration mode.

The endoscope system 10 having the above-mentioned configuration performs calibration as shown in FIG. 13 at a facility (a hospital or the like) where the endoscope system 10 is installed. In order to perform calibration, first, the endoscope system 10 is switched to the calibration mode by the operation of the mode changeover switch 13a of the endoscope 12. In a case where the endoscope system 10 is switched to the calibration mode, white light, illumination light for oxygen saturation, and green light G are sequentially emitted. In this state, the endoscope 12 is inserted into the calibration device 69 including the reference white plate WP. The image of the reference white plate WP is picked up in a state where the distal end part 12d of the endoscope faces the reference white plate WP. Then, in a case where the image pickup state of the reference white plate WP satisfies a certain condition, the static images of the reference white plate WP are acquired automatically or manually (by the operation of the freeze switch 13b). The static images of the reference white plate WP are transmitted to the calibration processing section 68.

The static images of the reference white plate WP include a B1 image, a G1 image, and an R1 image that are the spectral images of white light and a B2 image, a G2 image, and an R2 image that are the spectral images of illumination light for oxygen saturation. The calibration processing section 68 calculates predetermined statistics, such as the average values of the pixel values of the correction data acquisition regions AR, about the B1 image, the G1 image, the R1 image, and the B2 image among the static images of the reference white plate WP. Further, these statistics are stored in the white balance correction data storage section 70a as white balance correction data.

In a case where the white balance correction data are obtained, the linearity correction table-creation section 92 creates a linearity correction table using the B3 image and the G3 image subjected to white balance correction and the B3 image not yet subjected to white balance correction and stores this linearity correction table in the linearity correction table storage section 72a.

Figure 14:
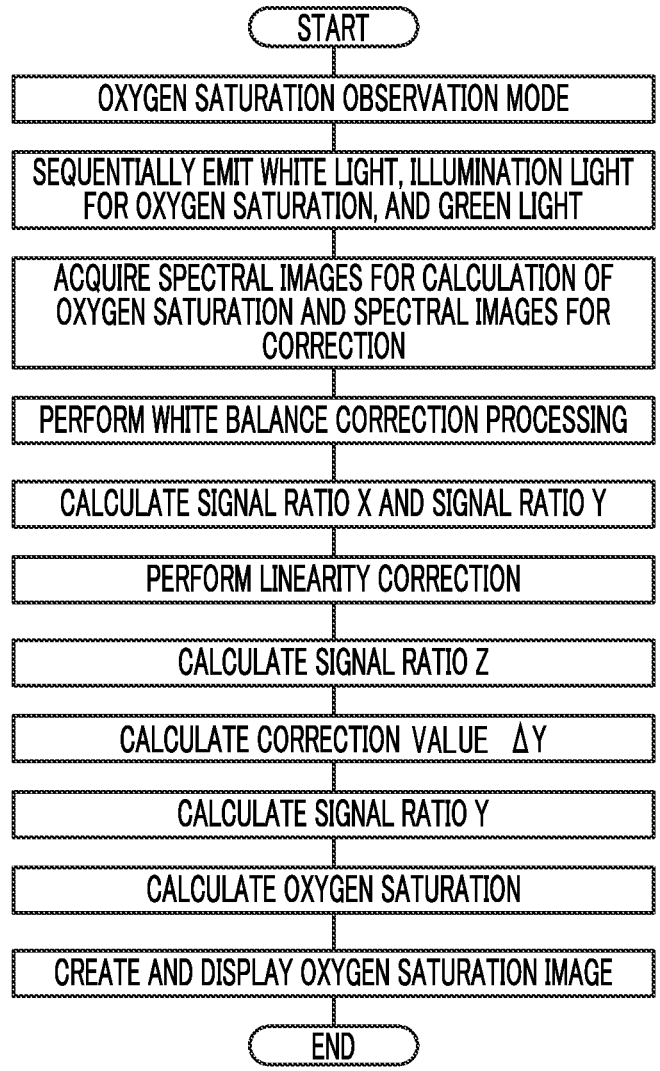
FIG. 14 is a flowchart of an oxygen saturation observation mode.

Further, the endoscope system 10 having the above-mentioned configuration operates as follows in the oxygen saturation observation mode. As shown in FIG. 14, first, the endoscope system 10 is switched to the oxygen saturation observation mode by the operation of the mode changeover switch 13a of the endoscope 12. In a case where the endoscope system 10 is switched to the oxygen saturation observation mode, white light, illumination light for oxygen saturation, and green light G are sequentially emitted. For this reason, the B1 image, the G1 image, and the R1 image, which are the spectral images for calculation of oxygen saturation, are acquired in the case of the image pickup frame of white light. The B2 image, the G2 image, and the R2 image, which are the spectral images for oxygen saturation, are acquired in the image pickup frame of illumination light for oxygen saturation. Then, the B3 image and the G3 image, which are the spectral images for correction, are acquired in the image pickup frame of green light G.

In a case where the respective spectral images are acquired as described above, the white balance correction processing section 70 performs white balance correction processing on at least the B1 image, the G1 image, the R1 image, the B2 image, the B3 image, and the G3 image. Accordingly, the B1 image, the G1 image, the R1 image, the B2 image, the B3 image, and the G3 image, which have been subjected to white balance correction, are obtained.

Next, the signal ratio calculation section 71 calculates the signal ratio X and the signal ratio Y using the B1 image, the G1 image, the R1 image, and the B2 image that have been subjected to white balance correction. On the other hand, the correction value calculation section 72 performs linearity correction on the B3 image, which has been subjected to white balance correction, with reference to the linearity correction table. Then, the correction value calculation section 72 calculates a signal ratio Z using the B3 image subjected to linearity correction. After that, the correction value calculation section 72 calculates the correction value $\Delta Y$, which is to be added to the signal ratio Y, using the signal ratio X, the signal ratio Y, and the signal ratio Z.

In a case where the correction value calculation section 72 calculates the correction value $\Delta Y$, the oxygen saturation calculation section 73 calculates oxygen saturation corresponding to a signal ratio Y*, which is a signal ratio Y in which the signal ratio Y and the correction value $\Delta Y$ are added to each other, for each pixel with reference to the correlation stored in the data storage section 73a for oxygen saturation. The image creation section 74 creates an oxygen saturation image using the calculated oxygen saturation. The created oxygen saturation image is displayed on the monitor 18.

As described above, the endoscope system 10 can correct an error, which is caused by the non-linear response characteristics of the image sensor 48, using the B3 image subjected to linearity correction and calculate accurate oxygen saturation. For example, in a case where the B3 image is not subjected to linearity correction, errors caused by the non-linear response characteristics of the image sensor 48 are included in the correction value ΔY. For this reason, even though the correction value ΔY is added to the signal ratio Y to correct the signal ratio Y, the errors caused by the non-linear response characteristics of the image sensor 48 remain. However, the above-mentioned endoscope system 10 reduces the errors caused by the non-linear response characteristics of the image sensor 48 at the time of the calculation of the correction value ΔY. As a result, accurate oxygen saturation can be calculated.

Further, the linearity correction, which is performed by the endoscope system 10, is to correct not only a difference in response characteristics (a difference in the model) caused by a difference in the model number of the image sensor 48 but also a non-linear individual difference in response characteristics caused by an individual difference occurring even in each image sensor 48 having a specific model number. Accordingly, since the endoscope system 10 can correct even a non-linear response that is the individual difference of the image sensor 48, the endoscope system 10 can more accurately calculate oxygen saturation as compared to, for example, an endoscope system in the related art that reduces merely a difference in the model of the image sensor 48 or the like.

The endoscope system 10 according to the embodiment can have a plurality of white balance correction data acquired by changing the emission intensity of illumination light while fixing a light emission ratio. Specifically, it is possible to acquire a plurality of white balance correction data "NB3a, NB3b, NB3c, . . . " for B3 image and a plurality of white balance correction data "NG3a, NG3b, NG3c, . . . " for G3 image by picking up the image of the reference white plate WP while changing the emission intensity of green light G whenever an image pickup frame in which green light G of the calibration mode is emitted is repeated. For example, NB3a and NG3a denote white balance correction data in a case where the amount of green light G is "a"; NB3b and NG3b denote white balance correction data in a case where the amount of green light G is "b"; and NB3c and NG3C denote white balance correction data in a case where the amount of green light G is "c".

In a case where the endoscope system 10 has the plurality of white balance correction data acquired while the emission intensity of illumination light is changed in this way, it is desired that the linearity correction table-creation section 92 creates a linearity correction table using these plurality of white balance correction data. The reason for this is to acquire data points at a plurality of points in the range AG3 of a value that can be taken by the pixel value of the G3 image not yet subjected to white balance correction and the range AB3 of a value that can be taken by the pixel value of the B3 image not yet subjected to white balance correction and to create a linearity correction table with high accuracy.

On the other hand, in a case where the endoscope system 10 picks up the image of the reference white plate WP using green light G only in one image pickup frame in the calibration mode, images for white balance correction to be obtained are one B3 image and one G3 image. In this case, in a case where one correction data acquisition region AR is set in each of the B3 image and the G3 image and the average values or the like of the pixel values of the correction data acquisition regions AR are defined as white balance correction data as in the embodiment, data can be obtained at only one point in the range AG3 of a value that can be taken by the pixel value of the G3 image not yet subjected to white balance correction and the range AB3 of a value that can be taken by the pixel value of the B3 image not yet subjected to white balance correction. For this reason, the accuracy of linearity correction using the linearity correction table may not be good depending on some specific response characteristics of the image sensor 48.

Figure 15:
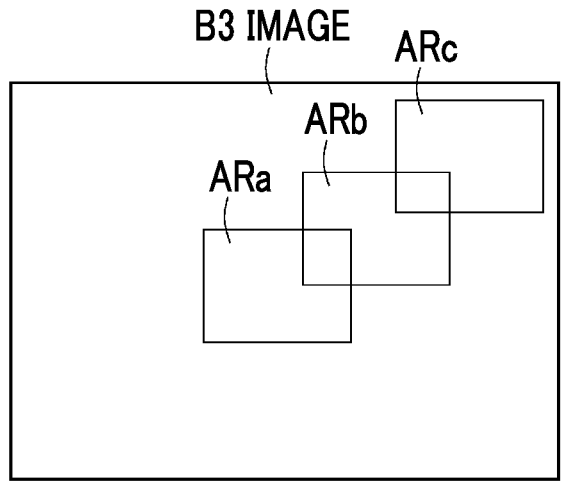
FIG. 15 is a diagram illustrating showing correction data acquisition regions of a modification example.

Accordingly, in a case where only one B3 image and one G3 image, which are images for white balance correction, are acquired, correction data acquisition regions AR are set at a plurality of positions in the B3 image and the G3 image. For example, a first correction data acquisition region ARa, a second correction data acquisition region ARb, and a third correction data acquisition region Arc are set in the B3 image as shown in FIG. 15. Then, the average value or the like of the pixel values in each of the first correction data acquisition region ARa, the second correction data acquisition region ARb, and the third correction data acquisition region Arc is calculated. After that, the average values or the like of the pixel values of the respective correction data acquisition regions ARa to Arc are defined as white balance correction data for B3 image. Accordingly, a plurality of white balance correction data "NB3a, NB3b, and NB3c" for B3 image are obtained. Likewise, a first correction data acquisition region ARa, a second correction data acquisition region ARb, and a third correction data acquisition region ARc are set even in the G3 image at positions corresponding to the above-mentioned positions, and the average values or the like of the pixel values of the respective correction data acquisition regions ARa to Arc are defined as white balance correction data for G3 image. Accordingly, first white balance correction data NG3a, second white balance correction data NG3b, and third white balance correction data NG3c are obtained.

Illumination light emitted from the endoscope 12 has an orientation and the distribution (orientation distribution) thereof is already known as structural characteristics of the endoscope 12. Accordingly, an image for white balance correction originally has a light-dark distribution and the aspect of the distribution is already known. For this reason, the first correction data acquisition region ARa, the second correction data acquisition region ARb, and the third correction data acquisition region Arc are different from each other in the average value or the like of brightness. Accordingly, different white balance correction data can be obtained in the first correction data acquisition region ARa, the second correction data acquisition region ARb, and the third correction data acquisition region Arc. The plurality of correction data acquisition regions ARa to Arc to be set in one image for white balance correction may partially overlap with each other or may be completely separated from each other. Further, the shapes of the plurality of correction data acquisition regions ARa to Arc are arbitrary and may be set to a circular shape or may be set to a rectangular shape as shown in FIG. 15. Furthermore, the plurality of correction data acquisition regions ARa to Arc may be circular and annular regions having concentric circles as boundaries.

In a case where the correction data acquisition regions ARa to Arc are set at a plurality of positions in the B3 image (or the G3 image), which is one image for white balance correction, and white balance correction data are acquired in each of the correction data acquisition regions ARa to ARc as described above, it is preferable that the linearity correction table-creation section 92 creates a linearity correction table using the plurality of white balance correction data acquired from this one image for white balance correction. Data points can be obtained at a plurality of points in the range AG3 of a value that can be taken by the pixel value of the G3 image not yet subjected to white balance correction and the range AB3 of a value that can be taken by the pixel value of the B3 image not yet subjected to white balance correction. As a result, a linearity correction table can be created with high accuracy.

Even in a case where a plurality of images for white balance correction are acquired while the emission intensity of illumination light is changed, a plurality of correction data acquisition regions ARa to Arc can be set in each of the images for white balance correction as described above. In a case where the plurality of images for white balance correction are acquired and the plurality of correction data acquisition regions ARa to Arc are set in each of the images for white balance correction, data points are obtained in more detail in the range AG3 of a value that can be taken by the pixel value of the G3 image not yet subjected to white balance correction and the range AB3 of a value that can be taken by the pixel value of the B3 image not yet subjected to white balance correction. For this reason, a linearity correction table can be created with particularly high accuracy, so that oxygen saturation can be particularly accurately calculated.

Linearity correction has been performed on the B3 image in the embodiment and the modification example. However, the reason for this is that there are many cases where the response characteristics of the image sensor 48 are non-linear response characteristics in the range AB3 of a value that can be taken by the pixel value of the B3 image not yet subjected to white balance correction. Accordingly, in a case where the response characteristics of the image sensor 48 are non-linear response characteristics in the range AG3 of a value that can be taken by the pixel value of the G3 image not yet subjected to white balance correction, linearity correction for the G3 image can be performed instead of linearity correction for the B3 image or together with linearity correction for the B3 image. In this case, a linearity correction table for G3 image is prepared in advance like the linearity correction table the B3 image of the embodiment or the like.

The correction value $\Delta Y$ is added to the signal ratio Y in the embodiment and the modification example, but the correction value calculation section 72 can obtain a correction value $\Delta Y$ that is to be multiplied or divided by the signal ratio Y. Further, the correction value calculation section 72 obtains the correction value $\Delta Y$ to be used to correct the signal ratio Y in the embodiment and the modification example, but can obtain a correction value $\Delta X$ to be used to correct the signal ratio X in the same way as a method of calculating the correction value $\Delta Y$ of the embodiment and the like.

The first color pixel is the B pixel and the second color pixel is the G pixel in the embodiment and the modification example, but the color (corresponding wavelength range) of each of the first color pixel and the second color pixel is arbitrary. For this reason, the first color pixel and the second color pixel can be a combination of pixels other than the B pixel and the G pixel of the embodiment and the modification example. However, it is preferable that the first color pixel corresponds to the amount of incident light and the range of a pixel value where the response characteristics of the image sensor 48 are non-linear, and the second color pixel corresponds to the amount of incident light and the range of a pixel value where the response characteristics of the image sensor 48 are substantially linear.

In the embodiment, an example of an endoscope system for a lumen using the endoscope 12, which is a soft endoscope, has been described as the endoscope system according to the embodiment of the present invention. However, the endoscope system according to the embodiment of the present invention can also be applied to an endoscope system for an abdominal cavity using a surgical rigid endoscope.

The hardware structures of the processing units, which execute various types of processing in the above description, such as the image acquisition unit 54, the image processing unit 61, the normal processing section 62, the special processing section 63, the display controller 66, the calibration processing section 68, the white balance correction processing section 70, the signal ratio calculation section 71, the correction value calculation section 72, the oxygen saturation calculation section 73, the image creation section 74, and respective parts of these, are various processors to be described below. The various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit (graphical processing unit: GPU)) that is a processor having circuit configuration designed exclusively to perform various types of processing; and the like.

One processing unit may be formed of one of these various processors, or may be formed of a combination of two or more same type or different types of processors (for example, a plurality of FPGAs, a combination of a CPU and an FPGA, or a combination of GPU and CPU). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by a system-on-chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined. Further, the hardware structure of the storage unit is a storage device, such as a hard disc drive (HDD) or a solid state drive (SSD).

EXPLANATION OF REFERENCES

10: endoscope system
12: endoscope
12a: insertion part
12b: operation part
12c: bendable part
12d: distal end part
12e: angle knob
13a: mode changeover switch
13b: freeze switch
13c: zoom operation part 14: light source device
16: processor device
18: monitor
19: user interface
20: light source unit
20a: BS light source
20b: BL light source
20c: G light source
20d: R light source
22: light source controller
30a: illumination optical system
30b: image pickup optical system
41: light guide
45: illumination lens
46: objective lens
47: zoom lens
48: image sensor
52: general controller
54: image acquisition unit
56: DSP
58: noise-reduction section
59: conversion section
61: image processing unit
62: normal processing section
63: special processing section
66: display controller
68: calibration processing section
69: calibration device
70: white balance correction processing section
70a: white balance correction data storage section
71: signal ratio calculation section
72: correction value calculation section
72a: linearity correction table storage section
73: oxygen saturation calculation section
73a: data storage section for oxygen saturation
74: image creation section
81: graph
82: graph
85: isoline
86: isoline
91: white balance correction data-creation section
92: linearity correction table-creation section
AB3: range
AG3: range
AR: correction data acquisition region
ARa: first correction data acquisition region
ARb: second correction data acquisition region
ARc: third correction data acquisition region
BF: blue color filter
BL: second blue light
BS: first blue light
f(B3): function
G: green light
GF: green color filter
QB3: ratio
R: red light
RF: red color filter
WP: reference white plate
X, Y: signal ratio

What is claimed is:

1. An endoscope system comprising:
an endoscope that includes an image sensor picking up an image of an object to be observed; and
a processor configured to:
use the endoscope to acquire a plurality of spectral images for calculation of oxygen saturation that are used to calculate oxygen saturation of the object to be observed and spectral images for correction that are used to calculate correction values to be used to correct the oxygen saturation;
calculate calculation values by calculation processing based on the plurality of spectral images for calculation of oxygen saturation;
create a linearity correction table that is used to linearize a relationship between an amount of light incident on the image sensor and pixel values of the spectral images for correction;
calculate the correction values using the calculation values and the spectral images for correction that have been subjected to linearity correction using the linearity correction table; and
calculate corrected calculation value using the calculation values and the correction values, and calculate the oxygen saturation based on the corrected calculation values with reference to a data storage section for oxygen saturation,
wherein an image to be subjected to linearity correction among the spectral images for correction is obtained from a first color pixel of the image sensor,
wherein an image among the spectral images for calculation of oxygen saturation is obtained from the first color pixel of the image sensor.

2. The endoscope system according to claim 1,
wherein the processor is further configured to:
calculate signal ratios, which are correlated with the oxygen saturation, from the plurality of spectral images for calculation of oxygen saturation;
calculate the oxygen saturation using the signal ratios; and
calculate the correction values that are used to correct the signal ratios.

3. The endoscope system according to claim 1,
wherein white balance correction data, which is used for correction of white balance, is provided, and
the processor is further configured to create the linearity correction table using the white balance correction data.

4. The endoscope system according to claim 3,
wherein the processor is further configured to create the linearity correction table in which a ratio between pixel values of a first color pixel and a second color pixel of the spectral image for correction subjected to white balance correction is associated with a pixel value of the first color pixel of the spectral image for correction not yet subjected to white balance correction.

5. The endoscope system according to claim 4,
wherein the first color pixel is a blue pixel and the second color pixel is a green pixel.

6. The endoscope system according to claim 5,
wherein the processor is further configured to create the linearity correction table using white balance correction data that are obtained in a case where an image of a reference plate is picked up using green light.

7. The endoscope system according to claim 6,
wherein the processor is further configured to cause a ratio between a pixel value of the first color pixel receiving the green light and a pixel value of the second color pixel receiving the green light to be associated with a pixel value of the first color pixel of the spectral image for correction not yet subjected to white balance correction.

8. The endoscope system according to claim 3,
wherein a plurality of the white balance correction data, which are acquired while emission intensity of illumination light is changed, are provided and, the processor is further configured to create the linearity correction table using the plurality of white balance correction data.

9. The endoscope system according to claim 3, wherein the processor is further configured to create the linearity correction table using a plurality of the white balance correction data acquired from one image for white balance correction, in a case where correction data acquisition regions are set at a plurality of positions in the one image for white balance correction and the white balance correction data are acquired in each of the correction data acquisition regions.

10. A method of operating an endoscope system including an endoscope that includes an image sensor picking up an image of an object to be observed, and a processor, the method comprising:

a step of causing the processor to use the endoscope to acquire a plurality of spectral images for calculation of oxygen saturation that are used to calculate oxygen saturation of the object to be observed and spectral images for correction that are used to calculate correction values to be used to correct the oxygen saturation;

a step of causing the processor to calculate calculation values by calculation processing based on the plurality of spectral images for calculation of oxygen saturation;

a step of causing the processor to create a linearity correction table that is used to linearize a relationship between an amount of light incident on the image sensor and pixel values of the spectral images for correction;

a step of causing the processor to calculate the correction values using the calculation values and the spectral images for correction that have been subjected to linearity correction using the linearity correction table; and a step of causing the processor to calculate corrected calculation value using the calculation values and the correction values, and calculate the oxygen saturation based on the corrected calculation values with reference to a data storage section for oxygen saturation, wherein an image to be subjected to linearity correction among the spectral images for correction is obtained from a first color pixel of the image sensor, wherein an image among the spectral images for calculation of oxygen saturation is obtained from the first color pixel of the image sensor.

* * * * *